(12) United States Patent
Gupta et al.

(10) Patent No.: US 9,795,281 B2
(45) Date of Patent: Oct. 24, 2017

(54) VARIABLE POWER ENDOSCOPE BASED ON LIQUID LENS TECHNOLOGY

(75) Inventors: Amitava Gupta, Roanoke, VA (US); Urban Schnell, Münchenbuchsee (CH); William Egan, Jackson, WY (US); Lisa Nibauer, Short Hills, NJ (US); Frank Stangota, Bridgewater, NJ (US); Julien Sauvet, Lyss (CH); Michel Saint-Ghislain, Düdingen (CH)

(73) Assignee: Adlens Beacon, Inc., Pembroke Park, FL (US)

( * ) Notice: Subject to any disclaimer, the term of this patent is extended or adjusted under 35 U.S.C. 154(b) by 0 days.

(21) Appl. No.: 13/309,269

(22) Filed: Dec. 1, 2011

(65) Prior Publication Data

US 2012/0143004 A1    Jun. 7, 2012

Related U.S. Application Data

(60) Provisional application No. 61/418,462, filed on Dec. 1, 2010.

(51) Int. Cl.
*G02C 7/08*    (2006.01)
*G02B 3/12*    (2006.01)
(Continued)

(52) U.S. Cl.
CPC ............ *A61B 1/0019* (2013.01); *A61B 1/002* (2013.01); *A61B 1/00096* (2013.01); *A61B 1/07* (2013.01);
(Continued)

(58) Field of Classification Search
CPC .................................... G02B 3/12; G02B 3/14
(Continued)

(56) References Cited

U.S. PATENT DOCUMENTS

| 4,181,408 A | * | 1/1980 | Senders | ................. A61B 3/113 359/666 |
| 4,261,655 A | * | 4/1981 | Honigsbaum | ............ G02B 3/12 359/666 |

(Continued)

FOREIGN PATENT DOCUMENTS

| JP | H05303011 A | 11/1993 |
| JP | 2010012172 A | 1/2010 |

(Continued)

OTHER PUBLICATIONS

Borish, I.M., *Clinical Refraction*, 3rd Edition, Chapter 26 (pp. 1051-1113), The Professional Press, Inc., Chicago (1970), 65 pages.

(Continued)

*Primary Examiner* — Timothy J Neal
*Assistant Examiner* — Aaron B Fairchild
(74) *Attorney, Agent, or Firm* — Greenberg Traurig, LLP

(57) ABSTRACT

An endoscope realized as either a borescope or a fiberscope including one or more fluid filled lenses is described. In an embodiment, the optical power of the fluid filled lenses may be adjusted to adjust the focal length associated with the endoscope. Thus, variable working distances are allowable while maintaining focus on an object in front of the endoscope. The endoscope may include a distance sensor, which is used to determine a distance between the endoscope and a sample. A processor may compare the measured distance to the current optical power of the one or more sealed fluid filled lenses. The processor may transmit signals to one or more actuators coupled to one or more sealed fluid filed lenses to change the optical power of the one or more sealed fluid filled lenses based on the comparison.

14 Claims, 8 Drawing Sheets

(51) Int. Cl.
*A61B 1/06* (2006.01)
*A61B 1/00* (2006.01)
*A61B 1/002* (2006.01)
*A61B 1/07* (2006.01)
*G02B 3/14* (2006.01)
*G02B 23/24* (2006.01)

(52) U.S. Cl.
CPC ............... *G02B 3/12* (2013.01); *G02B 3/14* (2013.01); *G02B 23/243* (2013.01); *G02B 23/2438* (2013.01); *G02C 7/085* (2013.01)

(58) Field of Classification Search
USPC .......... 600/167, 168, 160; 359/665, 666, 694
See application file for complete search history.

(56) References Cited

U.S. PATENT DOCUMENTS

| | | | | |
|---|---|---|---|---|
| 4,289,379 | A | * | 9/1981 | Michelet ................... 359/666 |
| 4,436,087 | A | * | 3/1984 | Ouchi ................ A61B 1/0008 600/160 |
| 4,913,536 | A | | 4/1990 | Barnea |
| 5,182,585 | A | * | 1/1993 | Stoner ..................... G02B 3/14 351/158 |
| 5,684,637 | A | | 11/1997 | Floyd |
| 5,973,852 | A | | 10/1999 | Task |
| 2004/0097790 | A1 | | 5/2004 | Farkas et al. |
| 2005/0270664 | A1 | | 12/2005 | Pauker et al. |
| 2007/0010707 | A1 | * | 1/2007 | Leiner et al. .............. 600/112 |
| 2007/0080280 | A1 | | 4/2007 | Havens |
| 2007/0280626 | A1 | | 12/2007 | Haddock et al. |
| 2008/0108873 | A1 | * | 5/2008 | Gattani et al. .............. 600/168 |
| 2009/0116118 | A1 | * | 5/2009 | Frazier ..................... G02B 3/14 359/666 |
| 2009/0195882 | A1 | * | 8/2009 | Bolle ....................... G02B 3/14 359/665 |
| 2009/0251792 | A1 | * | 10/2009 | Suzuki ..................... G02B 3/14 359/666 |

FOREIGN PATENT DOCUMENTS

| | | |
|---|---|---|
| KR | 20090103482 A | 10/2009 |
| WO | WO 2008/063442 A1 | 5/2008 |
| WO | WO 2011/047305 A1 | 4/2011 |

OTHER PUBLICATIONS

Jalie, M., *The Principles of Ophthalmic Lenses*, 4th Edition, Chapter 18, (pp. 413-468), The Association of Dispensing Opticians, Hazell Watson & Viney Limited, London (1984), 58 pages.

Markoff, J., "Scientists at Work: Stephen Kurtin—Making Eyeglasses That Let Wearers Change Focus on the Fly," *The New York Times*, 3 pages (Aug. 4, 2009).

Tang, S.K.Y. et al., "Dynamically Reconfigurable Liquid-Core Liquid-Cladding Lens in a Microfluidic Channel," *Lab on a Chip*, vol. 8, No. 3, p. 395-401 (Mar. 2008), 8 pages.

International Search Report and Written Opinion, dated Apr. 3, 2012, for PCT Appl. No. PCT/US11/62881, 11 pages.

* cited by examiner

VARIABLE POWER ENDOSCOPE BASED ON LIQUID LENS TECHNOLOGY

CROSS REFERENCE TO RELATED APPLICATIONS

This application claims priority to U.S. Provisional Patent Application No. 61/418,462 filed Dec. 1, 2010, which is incorporated herein by reference in its entirety.

BACKGROUND

Field

Embodiments of the present invention relate to fluid-filled lenses and in particular to variable fluid-filled lenses.

Background

Basic fluid lenses have been known since about 1958, as described in U.S. Pat. No. 2,836,101, incorporated herein by reference in its entirety. More recent examples may be found in "Dynamically Reconfigurable Fluid Core Fluid Cladding Lens in a Microfluidic Channel" by Tang et al., Lab Chip, 2008, vol. 8, p. 395, and in WIPO publication WO2008/063442, each of which is incorporated herein by reference in its entirety. These applications of fluid lenses are directed towards photonics, digital phone and camera technology and microelectronics.

Fluid lenses have also been proposed for ophthalmic applications (see, e.g., U.S. Pat. No. 7,085,065, which is incorporated herein by reference in its entirety). In all cases, the advantages of fluid lenses, such as a wide dynamic range, ability to provide adaptive correction, robustness, and low cost have to be balanced against limitations in aperture size, possibility of leakage, and consistency in performance. Endoscopes are optical tools which allow users to view areas where typical line-of-sight viewing is not feasible, such as areas within the body. An endoscope can be rigid, referred to more commonly as a borescope, or flexible, referred to usually as a fiberscope. Endoscopes typically contain a series of lenses along an optical path to provide an image of an object at one end of the endoscope to a user viewing through the other end of the endoscope. The use of conventional lenses within endoscopes defines a specific working distance at which the object being viewed is in focus. Deviating away from this working distance will cause the object to appear blurry to the user viewing it at the opposite end. Thus, the endoscope must be kept stationary at a certain distance away from an object in order to maintain clear focus of the object. Changing the working distance, or focal length, can be achieved by switching between lenses of various optical powers within the endoscope. However, once the endoscope is in use, it is very difficult to change any of the lenses used within it. Furthermore, only discrete working distances and magnification powers may be set using stationary lenses with rigid shapes.

BRIEF SUMMARY

In an embodiment, an endoscope includes a housing, one or more optical fibers, a sealed fluid filled lens, an actuator coupled to the sealed fluid filled lens, and a controller. The one or more optical fibers are disposed within the endoscope housing and provide a path for a light beam which intersects the fluid filled lens. The actuator is configured to change the optical power of the sealed fluid filled lens. The controller is configured to apply a signal to the actuator, wherein the signal instructs the actuator to change the optical power of the sealed fluid filled lens.

A method is described according to an embodiment. The method includes receiving a signal from a distance sensor. The signal received by the distance sensor is associated with a distance between a distal end of an endoscope and an object in front of the distal end of the endoscope. The method further includes comparing the received signal to the optical power of one or more sealed fluid filled lenses and to a requested magnification, and adjusting at least one of the optical power of the one or more sealed fluid filled lenses and the distance based on the comparing.

BRIEF DESCRIPTION OF THE DRAWINGS/FIGURES

The accompanying drawings, which are incorporated herein and form a part of the specification, illustrate embodiments of the present invention and, together with the description, further serve to explain the principles of the invention and to enable a person skilled in the pertinent art to make and use the invention.

Figure 3C:
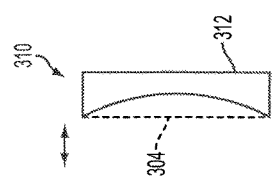
Figure 3B:
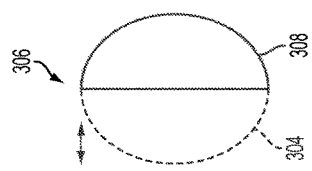
Figure 3A:
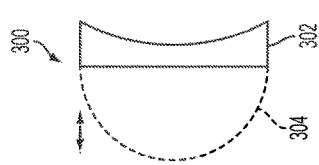

FIGS. 3A-C illustrate exemplary embodiments of a distal lens system that includes a fluid filled lens.

Figure 4:
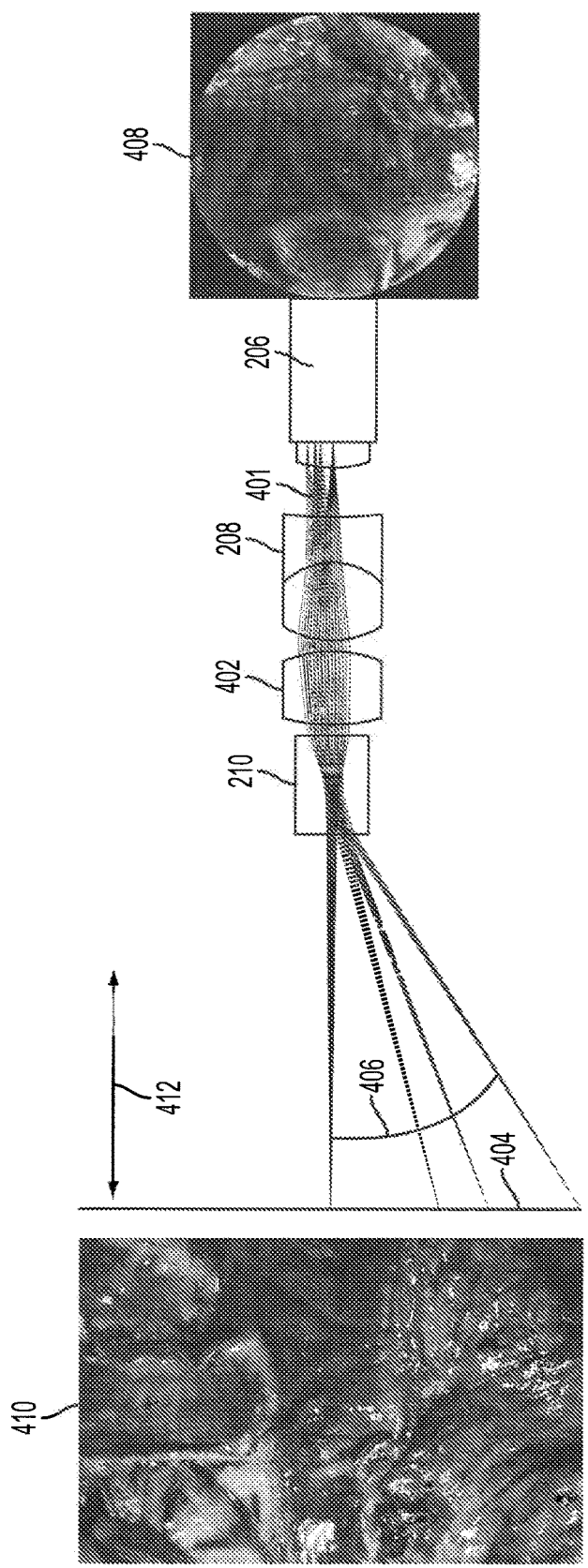

FIG. 4 illustrates the capturing of an object scene with an endoscope, according to an embodiment.

Figure 5:
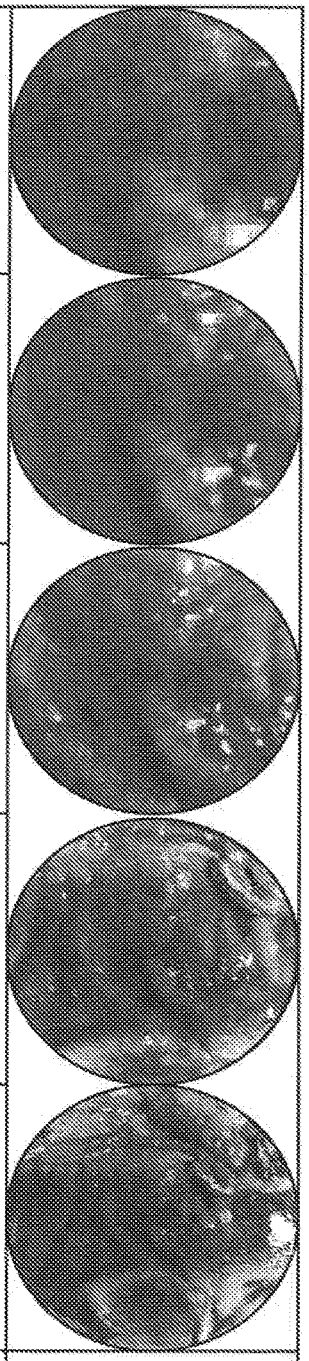

FIG. 5 displays a table showing simulated image results based on liquid lenses of varying curvature.

Figure 6:
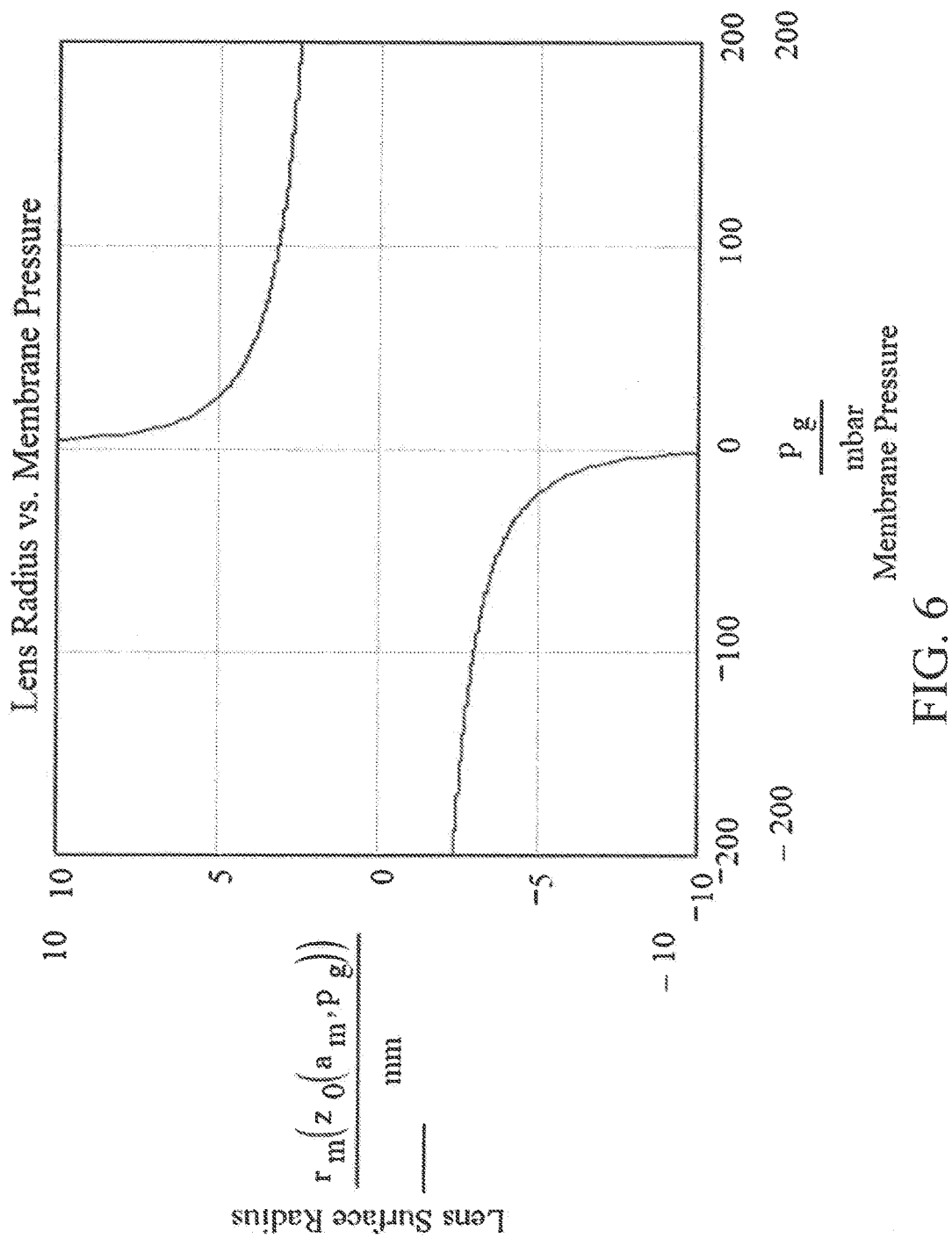

FIG. 6 displays simulation results in a graph of lens surface radius vs. applied membrane pressure, according to an embodiment.

Figure 7A:
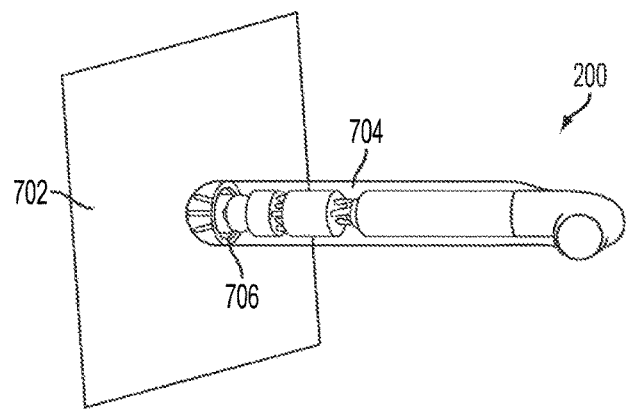
Figure 7B:
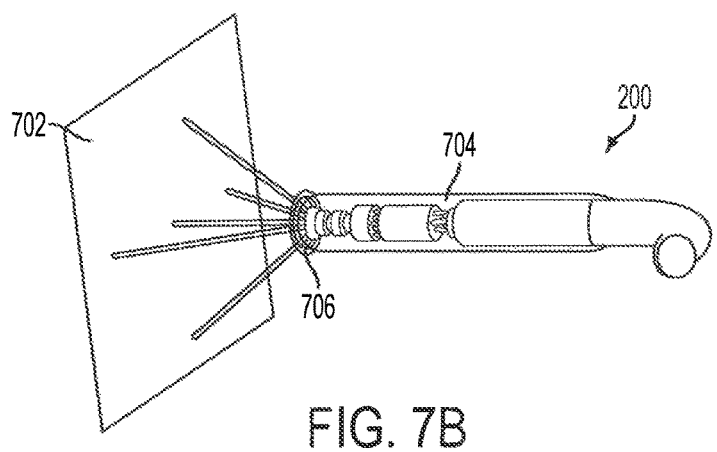
Figure 7C:
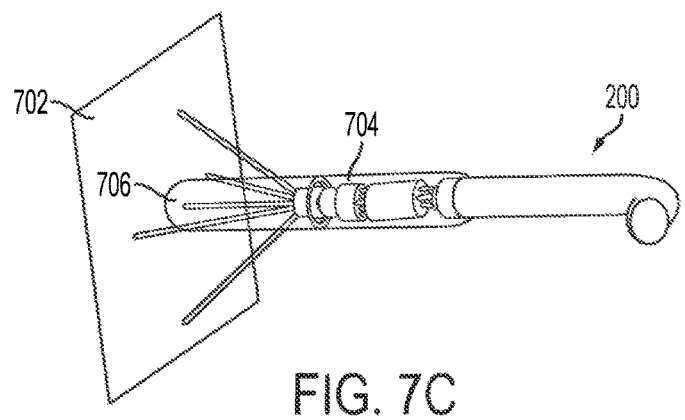

FIGS. 7A-C illustrate placements of the endoscope's optical components relative to a hermetic window and a sample surface, according to an embodiment.

Figure 8:
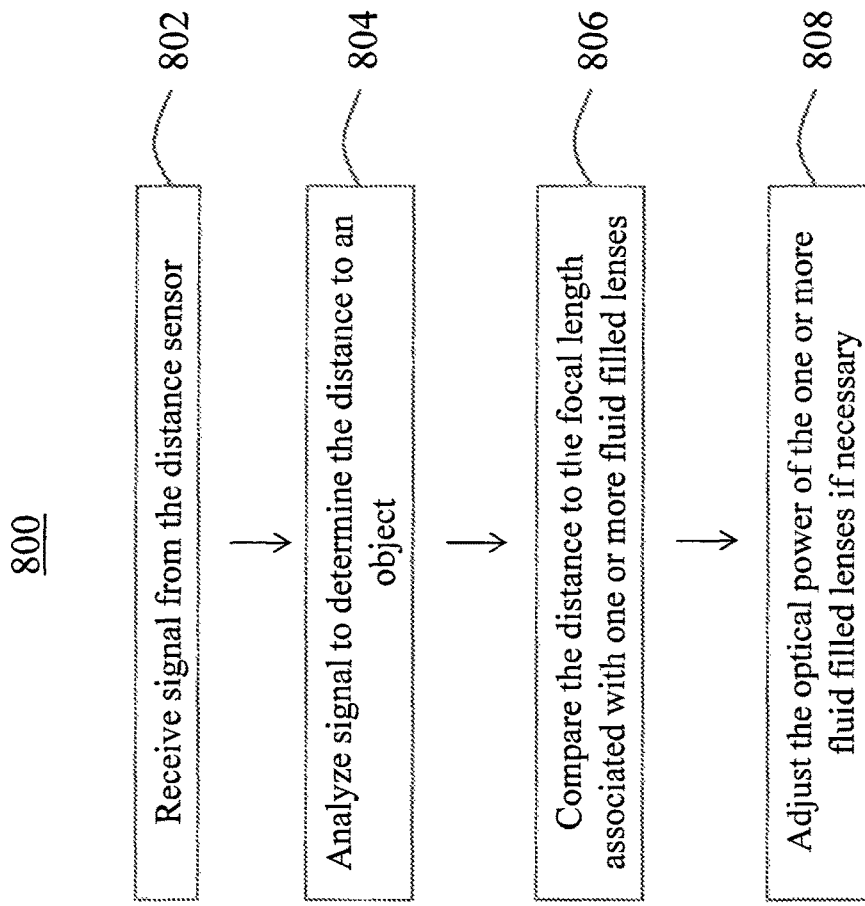

FIG. 8 is a diagram of a method, according to an embodiment.

Embodiments of the present invention will be described with reference to the accompanying drawings.

DETAILED DESCRIPTION

Although specific configurations and arrangements are discussed, it should be understood that this is done for illustrative purposes only. A person skilled in the pertinent art will recognize that other configurations and arrangements can be used without departing from the spirit and scope of the present invention. It will be apparent to a person skilled in the pertinent art that this invention can also be employed in a variety of other applications.

It is noted that references in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases do not necessarily refer to the same embodiment. Further, when a particular feature, structure or characteristic is described in connection with an embodiment, it would be within the knowledge of one skilled in the art to effect such feature, structure or characteristic in connection with other embodiments whether or not explicitly described.

Fluid lenses have important advantages over conventional, rigid lenses. First, fluid lenses are easily adjustable. Thus, according to an embodiment, an endoscope requiring additional positive power correction to view near objects may be fitted with a fluid lens of base power matching a particular distance. The user of the endoscope may then adjust the fluid lens to obtain additional positive power correction as needed to view objects at intermediate and other distances. Alternatively, the power may be corrected automatically as part of a feedback control loop as will be described in more detail later.

Second, fluid lenses can be adjusted continuously over a desired power range. As an example embodiment, the focal length associated with one or more fluid filled lenses within an endoscope may be adjusted to precisely match the distance between a distal end of the endoscope and an object in front of the distal end of the endoscope, allowing the user to move the endoscope closer or further from the object while maintaining focus.

Figure 1:
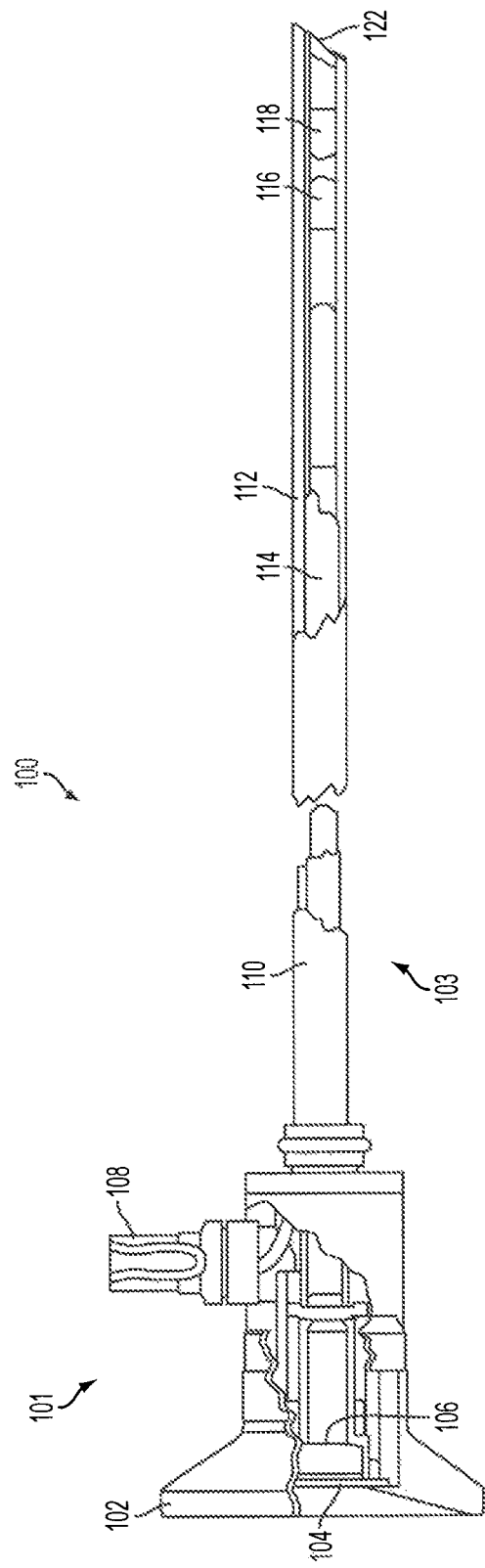
FIG. 1 illustrates an exemplary borescope, according to an embodiment.

FIG. 1 illustrates an embodiment of a borescope 100. Borescopes have a rigid structure along the path of the light within the borescope. They are commonly used in many industrial applications, for example, engine inspection, inspection of hazardous areas within chemical or nuclear plants, etc. Borescopes are also used during surgery to give the surgeon a better view within the body of a patient during the procedure. In an embodiment, borescope 100 includes an upper section 101 and a tubular section 103. A user typically handles borescope 100 with upper section 101 while tubular section 103 contains the optical elements which allow for the focusing and propagation of light.

Upper section 101 may include an eye shield 102, an ocular window 104, an eyepiece lens 106 and a light source 108. The user looks through ocular window 104 to view the light being received from a distal end 122 of borescope 100. In an embodiment, light source 108 is a broadband source. Alternatively, light source 108 may be a monochromatic source. The light propagating from light source 108 is coupled via focusing elements (not shown) into illumination fiber 112, according to an embodiment.

Tubular section 103 may include a housing 110, illumination fiber 112, an optical carrier tube 114, an objective lens 116, and a distal lens system 118 disposed at or near distal end 122. Housing 110 may be any rigid material such as stainless steel and also encompasses all optical components within tubular section 103, according to an embodiment.

Illumination fiber 112 may be a multi-mode, single-mode or polarization-mode fiber. Alternatively, a bundle of fibers may be used in place of illumination fiber 112. Carrier tube 114 contains the optical elements to provide a path for returning light to reach eyepiece lens 106, according to an embodiment. These optical elements may include glass rods with polished surfaces and indices of refraction so chosen as to minimize attenuation of the light.

Objective lens 116 is utilized to further focus light that has been transmitted through distal lens system 118, according to an embodiment. Distal lens system 118 may contain one or more fluid filled lenses which allow for variable tuning of the focal length and magnification associated with the lenses. This tunable aspect provides various working distances between distal end 122 and an object (not shown) to be used while maintaining focus upon the object as viewed at ocular window 104. Further description regarding the use of fluid filled lenses within distal lens system 118 will be explained later. It should be noted that borescope 100 may contain any number of other lenses for the purposes of modulating the pathway of the light.

In an embodiment, borescope 100 may include a distance sensor (not shown) coupled near distal end 122. In an embodiment, the distance sensor is attached to housing 110. The distance sensor transmits a signal and measures a return signal to determine a distance between distal end 122 and an object in front of distal end 122. The distance sensor may determine the distance based on comparing the amplitude of the transmitted signal to the amplitude of the returned signal. The amount of attenuation of the signal as it passes through the air or other fluid may be related to the distance traveled, assuming certain coefficients regarding the air or fluid are known, such as those associated with humidity. Alternatively, the distance sensor may act as an interferometer and determine the distance based on an interference signal generated by combining the return signal with a reference signal. The signals transmitted and received by the distance sensor may be any signals known by those skilled in the art for the purpose of measuring distance including, but not limited to, infrared, visible light, acoustic waves, etc.

Figure 2:
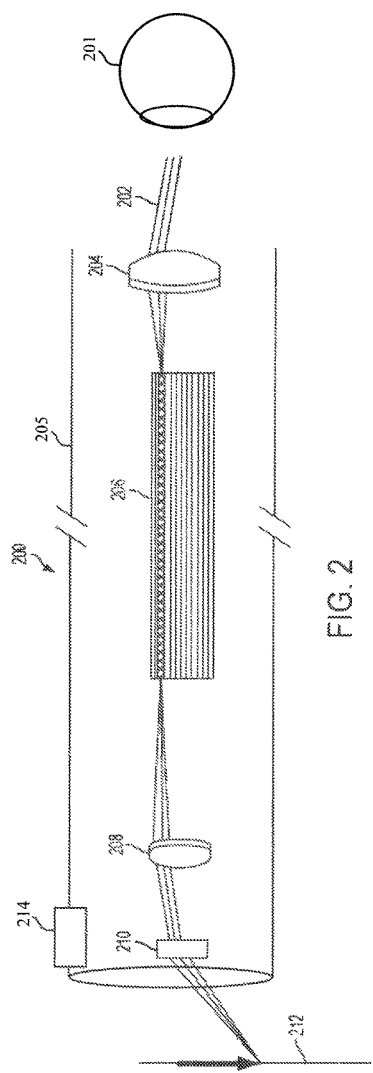
FIG. 2 illustrates an exemplary fiberscope, according to an embodiment.

FIG. 2 illustrates an embodiment of a fiberscope 200. Fiberscopes contain similar optical elements to borescopes, but utilize a bundle of optical fibers for all light transmission along the length of the fiberscope, allowing for much greater mechanical flexibility. Fiberscopes are often used during surgery, especially when moving through large organs, e.g. the colon. Fiberscope 200 includes an ocular lens 204, fiber bundle 206, objective lens 208 and distal lens system 210. Each of the elements may be disposed within a housing 205 which may consist of a flexible yet strong material to protect the optical elements within, such as polyethylene terephthalate (PET). Alternatively, housing 205 may be coupled to an end of fiber bundle 206 and encompass at least objective lens 208 and distal lens system 210.

It should be understood that distal lens system 210 of fiberscope 200 and distal lens system 118 of borescope 100 are to be considered synonymous and able to operate in the same fashion. Any description pertaining to one may be used to also describe the other.

In an embodiment, light 202 would be viewable by a user 201 through ocular lens 204. Light 202 is focused onto focal plane 212 via the optical components in the path of light 202 within fiberscope 200, according to an embodiment. If an object were disposed at focal plane 212, it would appear to be in focus to user 201. In another embodiment, light 202 is captured by a CCD camera positioned in front of ocular lens 204. The movement of focal plane 212 either closer or further from the distal end of fiberscope 200 depends on the optical powers associated with each of the lenses within the path of the light as well as their distance from one another. In an embodiment, distal lens system 210 contains one or more fluid filled lenses which allow for variable tuning of the focal length and magnification associated with the lenses. This tunable aspect provides various working distances between the distal end of fiberscope 200 and an object while maintaining focus upon the object.

Distal lens system 210 may include one or more fluid filled lenses and one or more rigid lenses. In an embodiment, the rigid lenses each contribute a constant optical power while the fluid filled lenses may adjust their optical power by applying fluid pressure on a membrane which alters the curvature of the lens.

Both ocular lens 204 and objective lens 208 may be of any shape and may be coupled with one or more other lenses for the purposes of modulating the path of light 202, according to an embodiment. Fiber bundle 206 may include any number of single-mode, multi-mode or polarization-mode fibers.

In an embodiment, fiberscope 200 may also include a distance sensor 214. Distance sensor 214 transmits a signal and measures a return signal to determine a distance between distal lens system 210 and an object in front of distal lens system 210. In one embodiment, distance sensor 214 is attached to the outer surface of housing 205 at or near distal lens system 210. In another embodiment, distance sensor 214 is attached to the inner surface of housing 205 at or near distal lens system 210. Distance sensor 214 may operate in the same manner as the distance sensor previously described for borescope 100.

FIGS. 3a-c illustrate side views of lens configuration embodiments within distal lens system 210. Each exemplary configuration includes an adjustable fluid filled lens and a rigid lens. The curvature of the fluid filled lens is altered to change the total optical power associated with the lens combination, i.e. optical power of the rigid lens (fixed)+ optical power of the fluid filled lens (variable).

FIG. 3a illustrates an exemplary first configuration 300, which includes a fluid filled lens 304 coupled to a plano-concave lens 302. Fluid filled lens 304 may be a fluid-filled membrane stretched over a rigid structure. In first configuration 300, the back of plano-concave lens 302 provides the rigid structure for fluid filled lens 304, according to an embodiment. The relatively low optical power associated with plano-concave lens 302 provides a long focal length which can be decreased depending on the curvature of fluid filled lens 304, according to an embodiment.

The curvature associated with fluid filled lens 304 causes light passing through to bend at an angle proportional to the imposed curvature. In an embodiment, the curvature of fluid filled lens 304 may be controlled via an electromechanical actuator (not shown) coupled to a fluid reservoir (not shown). The electromechanical actuator may apply a pressure to the fluid reservoir which forces fluid into fluid filled lens 304, thus decreasing the radius of curvature associated with fluid filled lens 304. The electromechanical actuator may also release pressure on the fluid reservoir to increase the radius of curvature associated with fluid filled lens 304. The electromechanical actuator may be a piezoelectric actuator as described in U.S. patent application Ser. No. 13/270,910 which is herein incorporated by reference in its entirety.

FIG. 3b illustrates an exemplary second configuration 306, which includes a fluid filled lens 304 coupled to a plano-convex lens 308. The relatively high optical power (compared to plano-concave lens 302) associated with plano-convex lens 308 provides a short focal length which can be further decreased depending on the curvature of fluid filled lens 304.

FIG. 3c illustrates an exemplary third configuration 310, which includes a fluid filled lens 304 coupled to the curved side of plano-concave lens 312. In an embodiment, fluid filled lens 304 in third configuration 310 may produce either positive or negative curvature due to the curved shape of the rigid structure over which the membrane is stretched. This may provide a greater tunable range of the optical power associated with the lens combination.

FIG. 4 illustrates an exemplary embodiment of an endoscope image acquired from a sample using a fiberscope. In an embodiment, the fiberscope includes elements described previously such as fiber bundle 206, objective lens 208 and distal lens system 210. The fiberscope may further include an additional optical lens 402. Light beams 401 are illustrated passing through the optical elements and impinging upon a focal plane 404, according to an embodiment. A working distance 412 describes the distance from focal plane 404 to the distal end of the fiberscope. According to an embodiment, distal lens system 210 is disposed at the distal end of the fiberscope. Half field-of-view angle 406 describes the highest angle at which light beams 401 exit from distal lens system 210. This angle is closely related to the magnification power associated with distal lens system 210. Higher magnifications result in a lower half field-of-view angle 406.

In an embodiment, object scene 410 displays a portion of an intestinal wall which is positioned at focal plane 404. In an embodiment, one or more fluid filled lenses within distal lens system 210 are tuned to adjust the focal length to equal working distance 412 so that object scene 410 is in focus. In another embodiment, one or more fluid filled lenses within distal lens system 210 are turned to adjust the magnification power to provide the desired magnification of object scene 410.

In an embodiment, endoscope image 408 displays what would be seen by a user or a CCD camera positioned at the proximal end of the endoscope.

FIG. 5 displays a table containing simulated images produced from an endoscope when varying the radius of curvature of a fluid filled lens within the endoscope, according to an embodiment. The table also provides values for the magnification power, half field-of-view angle, and working distance (focal length) associated with each change in the curvature. In an embodiment, the radius of curvature may indicate an effective radius of curvature produced by multiple lens components, e.g. a fluid filled lens with a radius of curvature of −1.8 mm may also be realized by a combination of one or more fluid filled lenses and one or more rigid lenses to modulate the path of the light in the same way as the single fluid filled lens with a radius of curvature of −1.8 mm.

A negative radius of curvature indicates a concave curvature, while a positive radius of curvature indicates a convex curvature. Additionally, the closer the number is to 0, the more extreme the curvature. Reading from left to right across the table, a fluid filled lens changes from a highly curved concave shape to a highly curved convex shape.

The change in the lens curvature affects the focal length and changes the working distance accordingly. In the simulated example, working distances range from 7.5 mm to 1 mm for a liquid lens radius of curvature of −1.8 mm to 1.1 mm respectively.

The simulation also shows an increase in the magnification power associated with the fluid filled lens system as the fluid filled lens moves towards a more convex shape, according to an embodiment. The increase in magnification is due to the changing distance between the membrane of the fluid filled lens and other optical elements coupled with the fluid filled lens as the membrane bulges outward. The half field of view angle decreases as the magnification increases since light is collected from a smaller portion of the object. In the simulated example, the half field of view angle varies from 32 degrees to 15 degrees for a liquid lens radius of curvature of −1.8 mm to 1.1 mm respectively.

In FIG. 5, images of a portion of an intestinal wall are displayed for each fluid filled lens radius of curvature. As the magnification increases, the simulated images provide closer inspection of the intestinal wall while maintaining enough contrast to distinguish particular features.

FIG. 6 displays a graph of simulation results for a fluid filled lens radius of curvature vs. applied membrane pressure. The simulation is performed assuming a fluid filled lens with a membrane radius of 0.2 mm and a thickness of 5 microns. The material properties of the membrane including Young's modulus, Poisson's ratio, etc., are chosen to be the same as those for polyethylene terephthalate (PET).

The results indicate that a minimum radius of curvature of 2.5 mm in either the positive or negative direction should be achievable for applied pressures higher than 200 mbar. In the simulated example, a radius of curvature varying from −2.5 mm to 2.5 mm corresponds to a change in magnification of 2× to 5×.

The simulation may also be performed using a different thickness or radius of fluid filled lens. For example, a membrane with a thickness of 1 micron can provide a magnification range of 1× to 8× when applying pressures up to 500 mbar.

FIGS. 7a-c illustrate exemplary positions of the components of fiberscope 200 relative to a sample surface 702. Sample surface 702 may be the surface of any object under inspection from fiberscope 200, such as, for example, the inner wall of a colon. FIG. 7a displays fiberscope 200 with a hermetic window 704 covering optical elements attached at the end of fiber bundle 206, according to an embodiment. Hermetic window 704 provides protection for the optical elements disposed within and is transparent to allow for the passage of optical signals, according to an embodiment. A distal end 706 of hermetic window 704 is placed against sample surface 702 while the optical elements are also positioned against sample surface 702 providing close inspection, according to the embodiment illustrated in FIG. 7a.

FIG. 7b displays fiberscope 200 pulled some distance away from sample surface 702 along with hermetic window 704, according to an embodiment. Thus, the movement of fiberscope 200 and hermetic window 704 are coupled and hermetic window 704 is considered to be fixed at the end of fiberscope 200, according to an embodiment.

FIG. 7c displays fiberscope 200 wherein the optical elements and fiber bundle 206 within hermetic window 704 may move independently of hermetic window 704. In an example, distal end 706 of hermetic window 704 is placed against sample surface 702 while the rest of fiberscope 200 has pulled some distance away from sample surface 702.

In an embodiment, the movement of fiber bundle 206 with the attached optical elements may be controlled via a slider connected to the housing (not shown) of fiberscope 200. In one example, a user may move the slider in order to translate fiberscope 200 either towards or away from sample surface 702 as illustrated in FIG. 7b. In another example, the user may move the slider in order to translate the optical elements and fiber bundle 206 within hermetic window 704 as illustrated in FIG. 7c.

FIG. 8 illustrates an exemplary lens control method 800, according to an embodiment.

At block 802, a signal is received from a distance sensor coupled near the end of an endoscope. The signal is related to a distance between the distance sensor and an object disposed in front of the distal end of the endoscope. Alternatively, the distance may be any value measured by the distance sensor. The signal may be received either electronically or optically from the distance sensor. A distance measurement may correspond to a particular voltage amplitude, AC frequency, or any other type of modulation as would be understood by one skilled in the art.

At block 804, the received signal is analyzed to determine the associated distance.

At block 806, the signal corresponding to a particular distance is compared to the current focal length associated with the distal lens system within the endoscope. The focal length associated with the distal lens system may be determined based on the optical power (directly related to curvature) of the one or more fluid filled lenses within the distal lens system. Using the exemplary distal lens system illustrated in FIG. 3a, if fluid filled lens 304 has an optical power of 0, then the focal length of the distal lens system is equal to the focal length associated with plano-concave lens 302 (or the reciprocal of the optical power associated with plano-concave lens 302). Alternatively, if fluid filled lens 304 has an optical power of 1.0, then the focal length of the distal lens system is equal to the focal length associated with both plano-concave lens 302 and fluid filled lens 304 (the reciprocal of the added optical powers of both plano-concave lens 302 and fluid filled lens 304).

The optical power of the one or more fluid filled lenses is also directly related to the curvature of the one or more fluid filled lenses. The curvature may be measured based on the amount of pressure applied by each actuator coupled to the one or more fluid filled lenses. In another embodiment, the curvature may be measured by an additional optical sensor. Alternatively, the curvature may be measured by a piezoresistive element.

At block 808, the optical power of the one or more fluid filled lenses is adjusted if necessary based on the comparison. In an embodiment, if the measured distance is equal to the focal length, then no adjustment is required. In a further embodiment, if the measured distance is within a certain threshold range of the focal length, no adjustment is required. However, if the measured distance is beyond a certain threshold range from the focal length, adjustment may be necessary to the optical power of the one or more fluid filled lenses. In one example, the adjustment is made by changing the curvature of the one or more fluid filled lenses.

If the measured distance is greater than a threshold range above the focal length, then the optical power of the one or more fluid filled lenses is reduced. The optical power may be reduced by transmitting a signal to an actuator to reduce pressure on a liquid reservoir associated with a fluid filled lens. The movement of liquid into the reservoir increases the radius of curvature of the associated fluid filled lens, and thus decreases its optical power.

If the measured distance is less than a threshold range below the focal length, then the optical power of the one or more fluid filled lenses is increased. The optical power may be increased by transmitting a signal to an actuator to increase pressure on a liquid reservoir associated with a fluid filled lens. The movement of liquid into the fluid filled lens decreases the radius of curvature of the associated fluid filled lens, and thus increases its optical power.

It should be understood that lens control method 800 may be stored as instructions on a computer readable storage medium and executed by a processor. Any computer readable storage medium may be used as would be known to those skilled in the art, including, but not limited to, RAM, flash memory, electronically erasable programmable read-only memory (EEPROM), hard disk drive, etc.

The pieces of the various endoscope embodiments described, for example, the housing, hermetic window, optical carrier tube etc, may be manufactured through any suitable process, such as metal injection molding (MIM), cast, machining, plastic injection molding, and the like. The choice of materials may be further informed by the requirements of mechanical properties, temperature sensitivity, optical properties such as dispersion, moldability properties, or any other factor apparent to a person having ordinary skill in the art.

The fluid used in the fluid filled lens may be a colorless fluid, however, other embodiments include fluid that is tinted, depending on the application, such as if the intended application is for sunglasses. One example of fluid that may be used is manufactured by Dow Corning of Midland, Mich., under the name "diffusion pump oil," which is also generally referred to as "silicone oil."

The fluid filled lens may include a rigid optical lens made of glass, plastic, or any other suitable material. Other suitable materials include, for example and without limitation, Diethylglycol bisallyl carbonate (DEG-BAC), poly(methyl methacrylate) (PMMA), and a proprietary polyurea complex, trade name TRIVEX (PPG).

The fluid filled lens may include a membrane made of a flexible, transparent, water impermeable material, such as, for example and without limitation, one or more of clear and elastic polyolefins, polycycloaliphatics, polyethers, polyesters, polyimides and polyurethanes, for example, polyvinylidene chloride films, including commercially available films, such as those manufactured as MYLAR or SARAN. Other polymers suitable for use as membrane materials include, for example and without limitation, polysulfones, polyurethanes, polythiourethanes, polyethylene terephthalate, polymers of cycloolefms and aliphatic or alicyclic polyethers.

A connecting tube between a fluid filled lens and a reservoir may be made ofone or more materials such as TYGON (polyvinyl chloride), PVDF (Polyvinyledene fluoride), and natural rubber. For example, PVDF may be suitable based on its durability, permeability, and resistance to crimping.

The various components of the endoscope embodiments, not including the optical fibers, may be any suitable shape, and may be made of plastic, metal, or any other suitable material. In an embodiment, the various housing components of the endoscope assembly are made of a lightweight material such as, for example and without limitation, high impact resistant plastics material, aluminum, titanium, or the like. In an embodiment, the components of the endoscope assembly may be made entirely or partly of a transparent material.

A reservoir coupled to the one or more fluid filled lenses may be made of, for example and without limitation, Polyvinyledene Difluoride, such as Heat-shrink VITON®, supplied by DuPont Performance Elastomers LLC of Wilmington, Del., DERAY-KYF 190 manufactured by DSG-CANUSA of Meckenheim, Germany (flexible), RW-175 manufactured by Tyco Electronics Corp. of Berwyn, Pa. (formerly Raychem Corp.) (semirigid), or any other suitable material. Additional embodiments of the reservoir are described in U.S. Pat. Pub. No. 2011/0102735 which is incorporated by reference in its entirety.

Any additional lenses beyond the described fluid filled lenses that may be included within the assembly of the endoscope embodiments may be of any sufficiently transparent material and may be in any shape, including but not limited to, biconvex, plano-convex, plano-concave, biconcave, etc. The additional lenses may be rigid or flexible.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. An endoscope, comprising:
    an endoscope housing;
    at least one optical fiber disposed within the endoscope housing and configured to provide a path for propagation of a light beam;
    at least one coupled lens system disposed in the endoscope housing and in the path of the light beam, wherein the at least one coupled lens system comprises:
    1) at least one rigid optical lens; and
    2) at least one sealed fluid filled lens, comprising:
        at least one flexible membrane member, and
        a face of the at least one rigid optical lens;
        wherein the at least one flexible membrane is directly stretched across the face of the at least one rigid optical lens;
        wherein the at least one rigid optical lens is made of at least one first material;
        wherein the at least one flexible membrane member is made of at least one second material;
    wherein the at least one first material is distinct from the at least one second material;
    at least one distance sensor attached to a distal end of the endoscope housing separated from the at least one coupled lens system, wherein the at least one distance sensor is configured to determine a distance between the distal end of the endoscope housing and an object in front of the distal end, and compare the distance with a focal length of the at least one sealed fluid filled lens;
    at least one actuator respectively coupled to the at least one sealed fluid filled lens and configured to receive a signal, based on the comparison, instructing the actuator to change optical power of the at least one sealed fluid filled lens; and
    at least one controller coupled to the at least one actuator and configured to operationally instruct the at least one actuator to change the optical power of the at least one sealed fluid filled lens.

2. The endoscope of claim 1, wherein the at least one distance sensor uses IR wavelengths.

3. The endoscope of claim 1, wherein the at least one distance sensor is an ultrasonic sensor.

4. The endoscope of claim 1, wherein the distance sensor uses visible light wavelengths.

5. The endoscope of claim 1, wherein the at least one controller operationally instructs the at least one actuator based on a measurement received from the distance sensor.

6. The endoscope of claim 1, wherein the at least one actuator is an electromechanical actuator.

7. The endoscope of claim 1, wherein the at least one actuator is configured to vary a pressure applied to a liquid reservoir coupled to the at least one sealed fluid filled lens.

8. The endoscope of claim 7, wherein the pressure applied changes a curvature of the at least one flexible membrane member of the at least one sealed fluid filled lens.

9. The endoscope of claim 8, wherein at least one change in the curvature of the flexible membrane member of the at least one sealed fluid filled lens changes a magnification of the at least one sealed fluid filled lens.

10. The endoscope of claim 9, wherein the at least one actuator is configured to change the magnification within the range of 2× to 5×.

11. The endoscope of claim 8, wherein the curvature has a minimum curvature radius equal to 2.5 mm.

12. The endoscope of claim 1, wherein the endoscope housing comprises a hermetic window, and wherein the at least one optical fiber, the at least one sealed fluid filled lens, the at least one rigid optical lens, and the at least one actuator are disposed within the hermetic window.

13. The endoscope of claim 1, wherein the housing further comprises a slider configured to move the at least one optical fiber, the at least one sealed fluid filled lens, the at least one rigid optical lens, and the at least one actuator along a length of the housing.

14. The endoscope of claim 1, wherein the at least one rigid optical lens is concave lens.

* * * * *